United States Patent [19]

Marshall, Sr. et al.

[11] Patent Number: 4,730,725
[45] Date of Patent: Mar. 15, 1988

[54] SUTURE TRAY

[75] Inventors: William M. Marshall, Sr., Salem; Nancy R. Gaut, Roanoke, both of Va.

[73] Assignee: MORF, Inc., Salem, Va.

[21] Appl. No.: 37,900

[22] Filed: Apr. 13, 1987

[51] Int. Cl.⁴ .............................................. A61L 17/02
[52] U.S. Cl. ................................. 206/63.3; 206/227; 206/380
[58] Field of Search ................... 206/63.3, 227, 380, 206/382, 381; 383/11

[56] References Cited

U.S. PATENT DOCUMENTS

| | | | |
|---|---|---|---|
| 2,176,452 | 10/1939 | Choffel | 206/63.3 |
| 2,724,208 | 11/1955 | Nelson | 43/57.5 |
| 3,388,790 | 6/1968 | Slomczewski | 206/63.3 |
| 3,529,649 | 9/1970 | Bennett | 383/11 |
| 3,647,057 | 3/1972 | Ashmead et al. | 206/17 |
| 3,779,375 | 12/1973 | Foster | 206/63.3 |
| 3,819,039 | 6/1974 | Erickson | 206/388 |
| 3,861,521 | 1/1975 | Burtz | 206/63.3 |
| 3,940,873 | 3/1976 | Lawless | 43/57.5 R |
| 3,985,227 | 10/1976 | Thyen et al. | 206/63.3 |
| 4,120,395 | 10/1978 | Mandel et al. | 206/63.3 |
| 4,135,623 | 1/1979 | Thyen | 206/63.3 |
| 4,151,913 | 5/1979 | Freitag | 206/370 |
| 4,182,448 | 1/1980 | Huck et al. | 206/63.3 |
| 4,183,431 | 1/1980 | Schmidt et al. | 206/63.3 |
| 4,418,733 | 12/1983 | Kallman | 383/11 |

Primary Examiner—Joseph Man-Fu Moy
Attorney, Agent, or Firm—John E. Benoit

[57] ABSTRACT

A tray for holding sutures, vessel loops, umbilical tapes, and the like, having a base with a substantially flat upper surface and a lip on one edge thereof for hooking onto a Mayo stand. The flt upper surface of the tray has secured thereto one side of a loop and hook fastener substantially adjacent each side thereof. A plurality of transparent covers are hinged to said base and have the other side of the loop and hook fastener secured thereto in mating fashion with the side of the fastener secured to the upper surface of the tray. Tabs extend outwardly from the tray so that sutures or the like may be looped about the tabs, with the ends protruding at the opposite end. When the transparent covers are folded down, the sutures are removably held by the loop and hook fastener.

7 Claims, 8 Drawing Figures

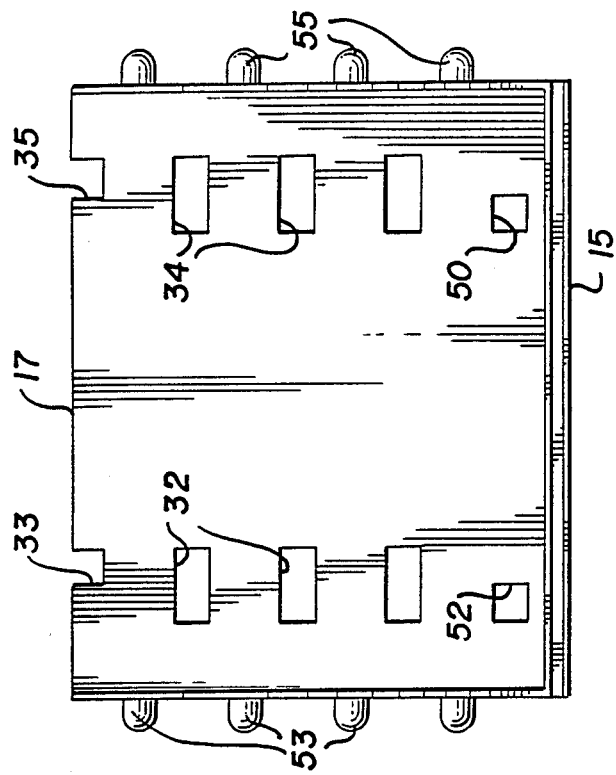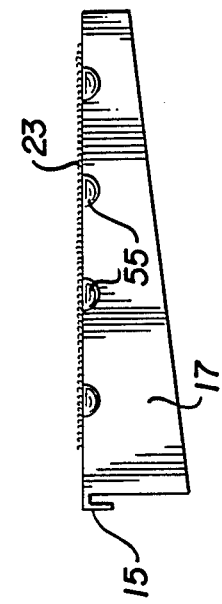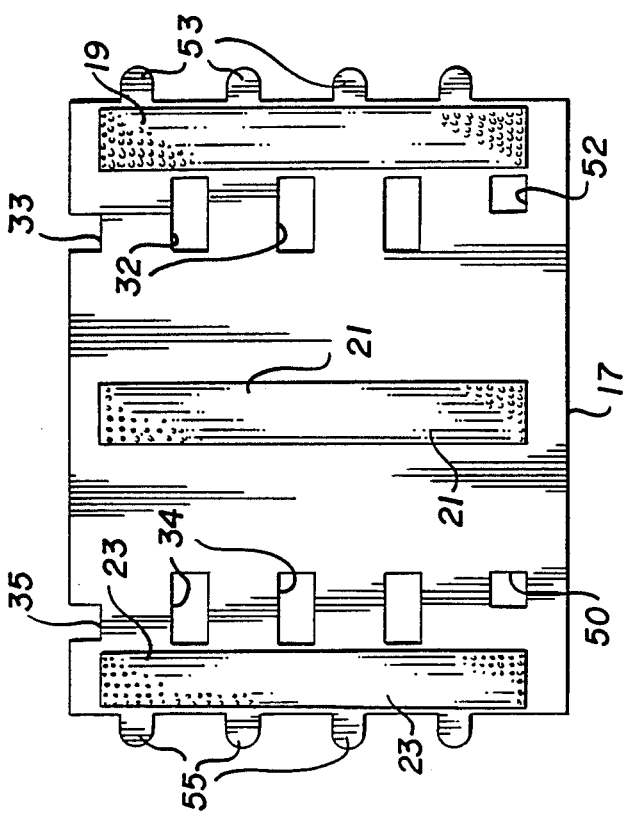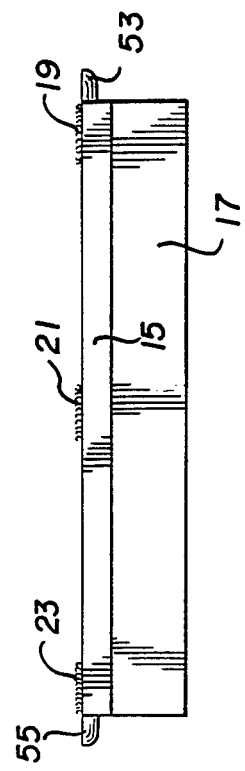

SUTURE TRAY

This invention relates generally to suture trays and, more specifically, to a suture tray having organized sutures, or the like, retained adjacent a surgery Mayo stand.

BACKGROUND OF THE INVENTION

During a surgical procedure, a Mayo stand is set up so as to hold instruments and other surgical supplies used most often during the surgery so that they may be readily available for use by the surgeon. The sterile Mayo stand is moved close to the surgical site so that the instruments and other supplies needed may be readily available to the surgeon without delay. When it is necessary for a scrub nurse to frequently turn away from the surgical site to obtain supplies from the sterile back table, the surgical procedure is inhibited and unnecessary time is wasted.

The present invention provides an organized place to keep items such as sutures, vessel loops, umbilical tapes, and the like, which are readily available for use without delay during the surgical procedure.

A further object of the invention is to provide a means whereby sutures and the like are readily available in different lengths and in different categories.

A further object of the invention is to provide a tray for sutures and the like which readily admit the insertion of further sutures into the tray.

Yet another object of the invention is to provide a tray for sutures and the like which are readily visible to the nurse and which may be removed individually without becoming entangled with the remaining sutures.

A still further object of the invention is to provide a sterile suture tray which is disposable after use.

These and other objects of the invention will become apparent from the following description, taken together with the drawings.

SUMMARY OF THE INVENTION

The present invention provides a disposable tray for holding sutures, vessel loops, umbilical tapes, and the like, which comprises a base having a substantially flat upper surface with one side of a loop and hook fastener secured to the flat upper surface adjacent opposed edges thereof. At least one transparent cover having a substantially flat underside is removably secured, preferably in a pivotal fashion, to the flat upper surface of the base. The other side of the hook and loop fastener is secured to the underside and the edges of the transparent cover in a mating location with the one side of said fastener on the flat upper surface of the base. Sutures and the like, such as vessel loops and umbilical tapes, can be laid across the base and extend outwardly therefrom so that when the covers are lowered onto the upper surface of the base, the sutures will be held in place but may be removed by pulling on either end thereof. The base may also include tabs extending outwardly therefrom so that longer sutures may be passed around the tab with both ends extending outwardly from the same end of the tray. As described above, the sutures may also be removed by pulling on one of the ends without disturbing any of the remaining sutures in the tray. The base and covers are formed of inexpensive plastic so that the tray may be discarded after use. The base includes a lip which mates with the rim of a Mayo stand so that the tray rests substantially perpendicular to the stand.

BRIEF DESCRIPTION OF THE DRAWING

FIG. 2 is a plan view of the upper surface of the base of FIG. 1;
FIG. 3 is a side view of the base of FIG. 1;
FIG. 4 is a bottom view of the base of FIG. 1;
FIG. 5 is an end view of the base of FIG. 1.

DETAILED DESCRIPTION OF THE PREFERRED EMBODIMENT

Figure 1:
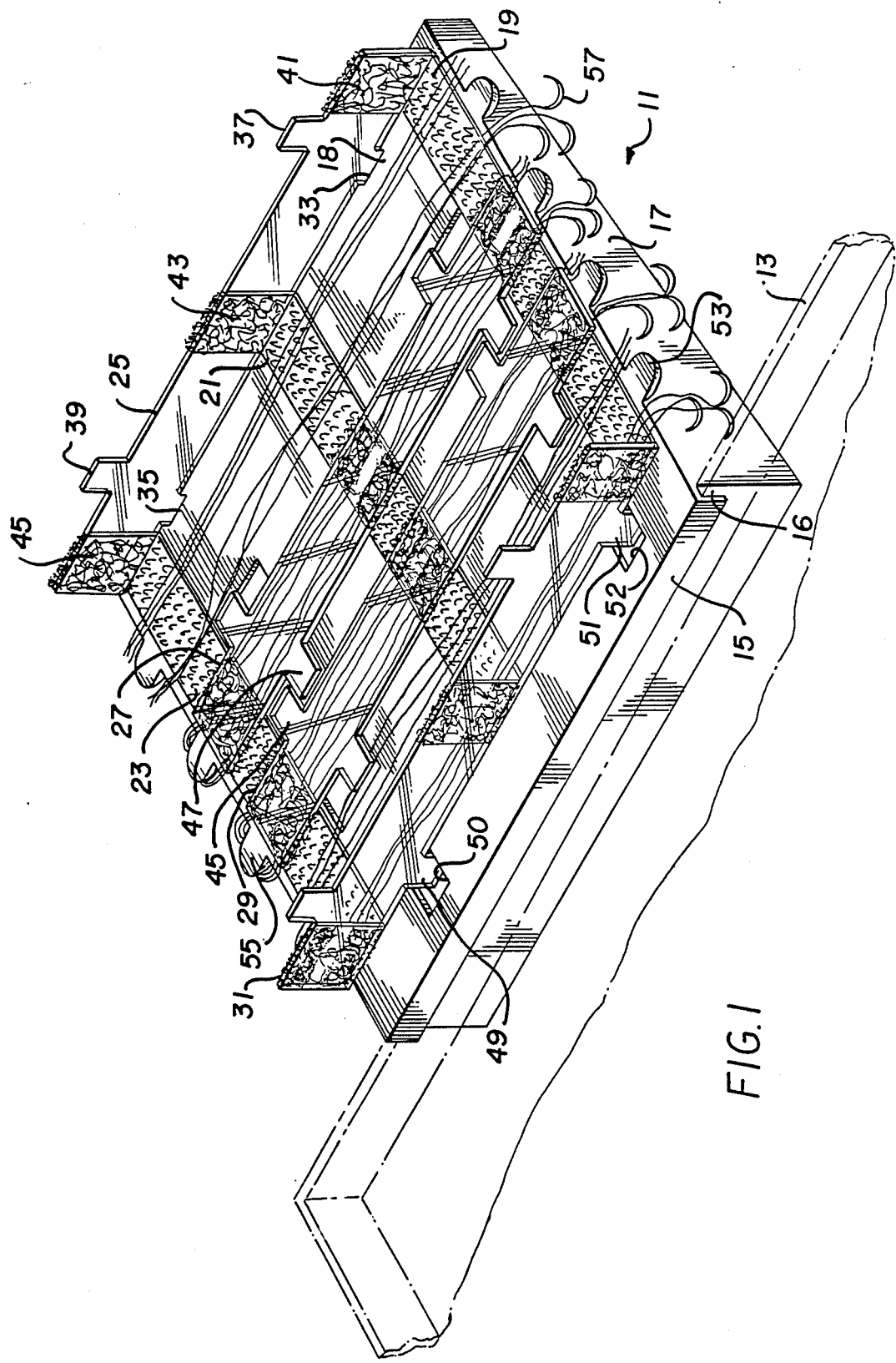
FIG. 1 is a perspective view of the tray of the present invention associated with a support means.
Figure 6:
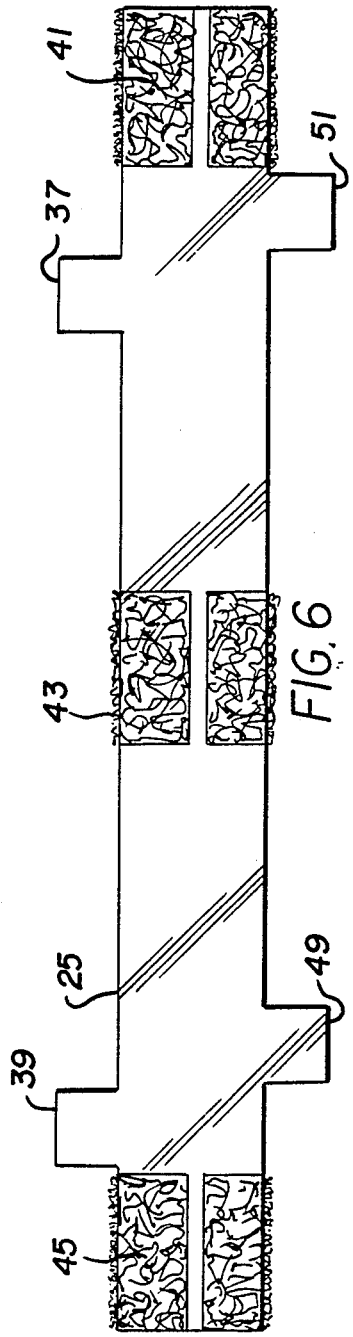
FIG. 6 is a plan view of the upper surface of one of the covers of FIG. 1.
Figure 7:
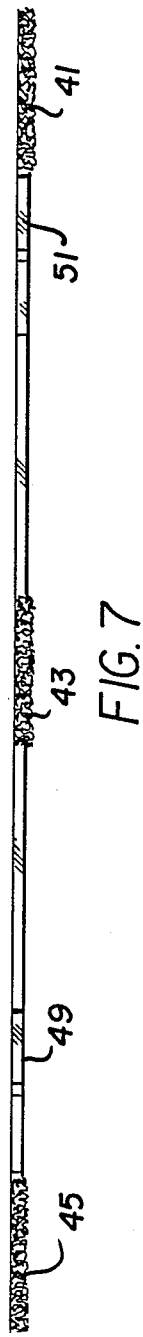
FIG. 7 is a side view of the cover of FIG. 6.
Figure 8:
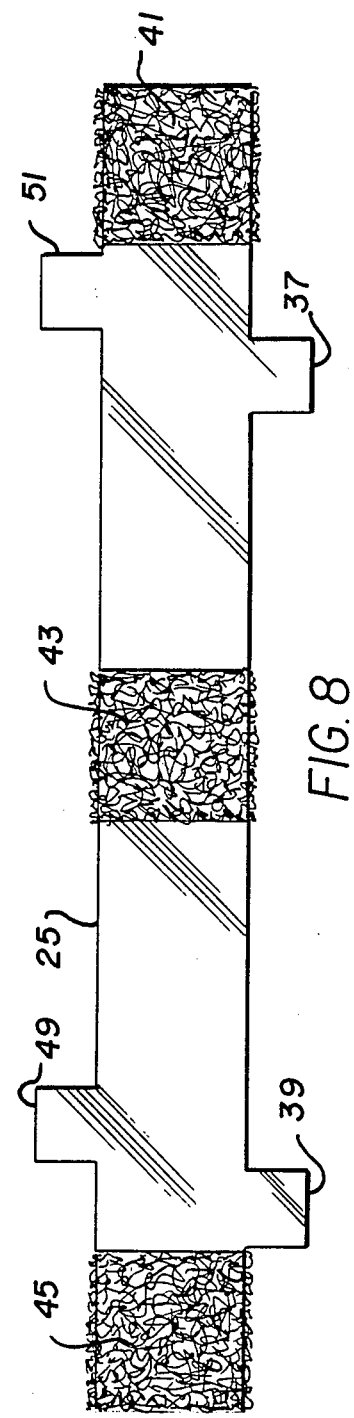
FIG. 8 is a plan view of the under surface of the cover of FIG. 6.

Turning now to the drawings, FIG. 1 is a perspective view of one embodiment of the suture tray of the present invention, while the remaining figures relate to the details of the base and the covers used in FIG. 1.

Suture tray 11 is shown in association with Mayo stand 13, partially indicated in dotted lines. Base 11 includes lip 15, which creates channel 16 adapted to fit over the rim of Mayo stand 13 so that the tray rests substantially perpendicular to the stand.

Secured to the upper flat surface 18 of base 17 are strips 19, 21, and 23. These strips constitute one section of a loop and hook type of fastener known by the trademark "Velcro." Although it does not matter which side is placed on the base, the loop side of such fastener is illustrated. A plurality of hinged covers 25, 27, 29, and 31 are removably hinged to the base at the upper surface thereof. The base includes slots such as slots 33, 35, 50, and 52, as well as intermediate slots 32 and 34. Each of the covers includes fingers 37 and 39 on one side and 49 and 51 on the opposite side. Since all of the covers are identical, only one will be described. Attention is directed to FIGS. 1, 6, 7, and 8.

Because of the dual finger arrangement, the covers may be hinged at either side. This is the reason why fingers on opposite sides are staggered so that they will not interfere with each other when lowered.

Each of the covers has on its underside and edges the other section of the hook and loop fasteners 41, 43, and 45. Such sections are shown extending substantially over the upper surface of the covers in FIG. 6. However, it is only essential that the bottom side and edges of the covers include the section of the hook and loop fastener in order to provide retention of the sutures and the hinge effect for the cover. These sections are located on the cover so as to mate with the sections on the upper flat surface of the base when the cover is closed downwardly. Since the section of the hook and loop fastener extends over the edges of the cover, the combination of the fingers resting in the slot and the loop and fastener contact create an effective pivot for the covers.

In the illustration of FIG. 1, the two outer covers are in their upward position, while the central covers are shown in their closed position.

A plurality of tabs 53 and·55 extend outwardly from base 17 adjacent the flat upper surface thereof. These tabs are used for long sutures which may be looped around the tabs on one side and extended to the other side where the ends protrude from the side beyond the covers. As illustrated under one of the covers, shorter sutures may be used which extend from either end of the upper surface of the base beneath the covers.

In order that the suture or like material may be clearly viewed when the covers are down and in place, it is preferable that these covers be transparent.

As will now be obvious, when the covers are in place, the loop and hook fasteners retain the sutures without allowing movement and yet permit withdrawal of the sutures by merely pulling on one end thereof. This permits the sutures to be withdrawn separately without disturbing the remaining sutures or becoming entangled therewith. As mentioned above, the term "sutures" is used broadly in that it may include the standard surgical sutures as well as vessel loops, umbilical tapes, and the like, which may be used during the surgical procedure.

Turning now to the operation and use of the suture tray, the sterile packaged suture tray is opened and given to the scrub nurse. The Mayo stand is draped with a sterile cover and the suture tray is attached to the Mayo stand as disclosed and illustrated in FIG. 1. At that time, the scrub nurse completes the set-up of the Mayo stand and the suture tray.

Sutures needed for the surgical procedure are placed under the hinged covers of the suture tray so as to keep them separated and organized until needed by the surgeon. As stated, the suture tray will also accommodate vessel loops and umbilical tape in the same manner.

Once the patient is prepped and draped and the sterile field is prepared, the sterile Mayo stand, with the suture tray attached, is moved to the sterile field. As the operation proceeds, the scrub nurse may quickly and easily supply the surgeon with the appropriate suture needed since the suture tray keeps these sutures separated and organized and enables one suture to be removed without disturbing or entangling the remaining sutures. As will be obvious, this enhances the harmonious process of the procedure without unnecessary delay.

Because the suture tray is attached to the Mayo stand, the scrub nurse does not have to turn her attention away from the sterile field to obtain sutures needed by the surgeon. Turning away from the operative field is considered bad technique and extends the time of the surgical procedure.

Because the hinged covers of the suture tray are transparent, the scrub nurse continually monitors her supply of sutures. As additional sutures are needed they may be added to the suture tray quickly and easily since raising one hinged cover does not disturb sutures under the other hinged covers.

As indicated above, the suture tray will accommodate sutures of different lengths. Eighteen-inch sutures fit under the hinged covers with both ends hanging slightly over either edge. Sometimes there is a need for longer sutures, such as 30-inch sutures. These sutures are doubled and looped around a tab at either end of the hinged cover, with the loose ends hanging over the edge at the opposite side in the same manner as the shorter sutures. Certain types of sutures come in a multi-pack with swaged-on needles. These may also be placed under the hinged covers and removed one at a time, as needed.

Since the tray and covers are molded from an inexpensive plastic, once the surgical procedure is completed the suture tray is simply disposed of along with other disposable surgical supplies used during the surgical procedure.

The above description and drawings are illustrative, only, since modifications may be made in the structure without departing from the invention, the scope of which is to be limited only by the following claims.

We claim:

1. A tray for holding sutures, vessel loops, umbilical tapes, and the like, comprising
   a rigid base having a substantially flat upper surface;
   a lip integral with said base, said lip being spaced from and extending downwardly from an edge of said flat upper surface;
   one side of a loop and hook fastener secured to said flat upper surface adjacent opposed edges thereof;
   at least one cover having a substantially flat underside of substantially the same dimensions as said upper surface;
   means for removably inserting one edge of said cover into said flat upper surface, said cover being pivotable relative to said upper surface; and
   the other side of said hook and loop fastener being secured to said underside and edge of said cover in a mating location with said one side of said fastener.

2. The tray of claim 1 wherein said cover is transparent.

3. The tray of claim 1 further comprising
   one side of a further loop and hook fastener secured to said flat upper surface substantially centrally between opposed edges thereof, and a further other side of a loop and hook fastener being secured to said underside of said cover in a mating location with said one side of said further loop and fastener.

4. The tray of claim 1 further comprising
   a plurality of substantially parallel covers extending between said opposed edges of said flat upper surface.

5. The tray of claim 1 further comprising at least one tab extending outwardly from at least one of said opposed edges of said flat surface.

6. The tray of claim 1 further comprising a plurality of tabs extending outwardly from at least one of said opposed edges of said flat surface.

7. The tray of claim 1 wherein said base and said cover are of a molded plastic.

* * * * *